United States Patent [19]
Glenn et al.

[11] Patent Number: 5,886,038
[45] Date of Patent: Mar. 23, 1999

[54] COMPOSITION AND METHOD FOR TREATMENT OF PSORIASIS

[75] Inventors: Thomas M. Glenn, Houston, Tex.; E. William Rosenberg; Robert B. Skinner, Jr., both of Memphis, Tenn.; Patricia W. Noah, Germantown, Tenn.

[73] Assignees: Panda Pharmaceuticals, L.L.C., Memphis; The University of Tennessee Research Corporation, Knoxville, both of Tenn.

[21] Appl. No.: 46,851

[22] Filed: Mar. 24, 1998

[51] Int. Cl.⁶ .................................................. A61K 31/32
[52] U.S. Cl. ............................................ 514/552; 514/863
[58] Field of Search ................................... 514/552, 863

[56] References Cited

U.S. PATENT DOCUMENTS

| | | | |
|---|---|---|---|
| 4,316,902 | 2/1982 | Yu et al. | 424/266 |
| 4,495,203 | 1/1985 | Grollier et al. | 514/732 |
| 4,496,588 | 1/1985 | Bey et al. | 514/564 |
| 4,507,321 | 3/1985 | Raisfeld | 514/673 |
| 4,513,011 | 4/1985 | Grollier et al. | 514/730 |
| 4,518,789 | 5/1985 | Yu et al. | 560/105 |
| 4,847,257 | 7/1989 | Hupe et al. | 514/269 |
| 4,933,330 | 6/1990 | Jorgensen et al. | 514/159 |
| 4,981,681 | 1/1991 | Tosti | 424/78 |

OTHER PUBLICATIONS

Federal Register, vol. 47, No. 233, Part IV, Department of Health and Human Services, FDA, OTC Drug Products for the Control of Dandruff, Seborrheic Dermatitis, and Psoriasis; Establishment of a Monograph, Dec. 3, 1982, pp. 54646–54684.

"A Super–Effective Natural Therapy for Psoriasis", *Health & Healing*, vol. 7, No. 2, By Dr. Julian Whitaker, Feb. 1997, pp. 4–5.

*The Schoch Letter*, vol. 47, No. 4, Editor: Ervin Epstein, Apr. 1997, Paragraphs 49, 50.

"Psoriasis Patients Try the Alternatives", *Skin & Allergy News*, vol. 28, No. 3, dated prior to Mar. 18, 1997, pp. 1 & 25.

*1997 CIR Compendium*, Cosmetic Ingredient Review, Washington, D.C., 1997, p. 97.

*Primary Examiner*—Leonard Schenkman
*Attorney, Agent, or Firm*—Pearne, Gordon, McCoy & Granger LLP

[57] ABSTRACT

A pharmaceutical composition for use in the treatment of psoriasis, having isopropyl myristate as its only active ingredient.

9 Claims, No Drawings

5,886,038

COMPOSITION AND METHOD FOR TREATMENT OF PSORIASIS

FIELD OF THE INVENTION

This invention relates to pharmaceutical compositions and more particularly to a pharmaceutical composition for use in the treatment of psoriasis.

DESCRIPTION OF RELATED ART

Psoriasis is a chronic skin disease or condition characterized by circumscribed red patches covered with white scales. Conventional treatment compositions include corticosteroid, calcipotriol, and retinoid creams. Coal tar, salicylic acid, zinc pyrithione, and anthralin compositions are also known. U.S. Pat. Nos. 4,513,011; 4,495,203; 4,507,321; 4,933,330; 4,847,257; 4,496,588; 4,981,681; and 4,518,789, the contents of which are incorporated herein by reference, disclose compositions for the treatment of psoriasis. See also U.S. FDA OTC Drug Monograph, Federal Register, Vol. 47, No. 233 (Dec. 3, 1982) pp. 54646–54684, the contents of which are incorporated by reference, which lists OTC compositions for treatment of psoriasis.

Isopropyl myristate has been known as an excipient or vehicle for cosmetic creams and topical medicinals for many years, particularly where good absorption through the skin is desired. However, isopropyl myristate has not been known as an active ingredient or agent for the treatment of psoriasis. There is a need for an effective, less complex, less costly composition for the treatment of psoriasis.

SUMMARY OF THE INVENTION

A pharmaceutical composition for use in the treatment of psoriasis comprising isopropyl myristate, said isopropyl myristate being the only active ingredient for the treatment of psoriasis in the composition. The pharmaceutical composition is in a form suitable for topical administration to a human and is selected from the group consisting of a cream, an ointment, a lotion, a liniment, a gel, a solution, a suspension, a paste, a stick, a spray, an aerosol, a shampoo, a soap, a hair conditioner, and a powder. The invention also includes a method of using the composition to treat psoriasis.

DETAILED DESCRIPTION OF THE PREFERRED EMBODIMENTS OF THE INVENTION

As used herein, parts are parts by weight and percents are weight percents unless otherwise indicated or apparent. When a preferred range such as 5–25 is given, this means preferably at least 5 and preferably not more than 25.

The isopropyl myristate active ingredient is supplied in a pharmaceutically acceptable vehicle for topical administration. Such topically acceptable pharmaceutical compositions include a cream, an ointment, a lotion, a liniment, a gel, a solution, a suspension, a paste, a stick, a spray, an aerosol, a shampoo, a soap, a hair conditioner, and a powder. The composition of these vehicles is conventional and known in the art. The invented composition has the following preferred formulation, which is applied by pump spray.

| | INGREDIENT | PREFERRED WEIGHT PERCENT (Formulation A) | LESS PREFERRED WEIGHT PERCENT | LESS PREFERRED WEIGHT PERCENT (Formulation B) | LESS PREFERRED WEIGHT PERCENT |
|---|---|---|---|---|---|
| 1. | Isopropyl myristate | 40 | 38–60 | 25 | 15–90 |
| 2. | Sodium/lauryl sulphate | 0.1 | 0.05–0.2 | 0.125 | 0–2 |
| 3. | Polysorbate 80 | 1.5 | 0.8–2 | 1.875 | 0–5 |
| 4. | Water | 3.4 | 1.5–10 | 4.25 | 0.8–60 |
| 5. | Ethanol | 55 | 35–60 | 68.75 | 5–75 |

Isopropyl myristate is the only active ingredient for the treatment of psoriasis in this formulation and is the only active ingredient in the invented pharmaceutical compositions. All the other ingredients are inert or inactive against psoriasis. In the above formulations Ingredients 2–5 form the vehicle or vehicle system or carrier or carrier system. Isopropyl myristate is preferably present in a weight percent of at least 15, 20, 25, 30, 35, 40, 45, 50, 55, or 60 weight percent and preferably not more than 55, 60, 65, 70, 75, 80, 85, 90 or 95 weight percent. In less preferred formulations isopropyl myristate may be present in 98 or 99 or, less preferably, 100 weight percent.

Sodium lauryl sulphate and Polysorbate 80 (polyoxyethylene (20) sorbitan monooleate) are emulsifiers (also sometimes referred to as dispersants or surfactants) to help solubilize or emulsify or disperse the isopropyl myristate in the vehicle. Isopropyl myristate is very soluble or miscible in ethanol and when the vehicle is predominantly ethanol or other alcohol, the emulsifiers may be unnecessary and omitted. As water forms a greater percent of the vehicle, emulsifiers may be necessary to emulsify or solubilize the isopropyl myristate. Suitable emulsifiers are known in the art, including the various Tween compounds, the various ethanolamines such as triethanolamine, the various SPAN compounds, dioctyl sodium sulfosuccinate, Celouacrogols, Tensides, etc. These emulsifiers may be used singlely or in combination. The emulsifiers preferably form less than 3 or 5 or 10 weight percent of the formulation.

In the formulation above the vehicle is preferably a combination of water and alcohol, such as 25/75, 50/50, or 75/25 water to alcohol (w/w). The vehicle may optionally be all water (emulsifiers as needed) or all alcohol, or any combination inbetween. For example, the vehicle may be at least or at most or equal to 10, 20, 30, 40, 50, 60, 70, 80, or 90 weight percent water, with the balance alcohol, and emulsifiers as needed. The more water, the greasier the formulation. The more alcohol, the greater the formulation will dry out the skin. Both extremes should be avoided. Emollients, humectants, and other customary additives may be added. Sufficient water should be added (such as at least 3, 5 or 8 weight percent) to prevent the alcohol from unduly drying the skin, and to reduce the flammability of the vehicle. The flash point will be reduced, making the product less hazardous to make and use.

Ethanol, preferably 96% ethanol, is the preferred alcohol. Less preferably isopropyl alcohol may be used or other common alcohols, or combinations thereof. Preferably at least 25, 30, 35, 40, 45, 50, 55, or 60 weight percent of the composition is formed from water, ethanol, isopropyl alcohol, or any combination thereof, preferably the combination of water and ethanol.

Less preferably the isopropyl myristate active ingredient, preferably in the concentrations or weight percents noted above or in weight percents appropriate considering the weight percents above and weight percents customary in the other vehicles, may be provided to the patient in other pharmaceutically acceptable vehicles for topical administration known in the art. For example, the vehicle may be an oil system, such as fat or oil or synthetic fat such as petrolatum. The vehicle may be (1) a lotion, such as water and fat or oil with an emulsifier and with or without a little ethanol (with customarily a lower concentration of the active ingredient); (2) a cream or cream base, which is generally the same as a lotion but with less water and a higher viscosity and customarily a higher concentration of the active ingredient; (3) an ointment, which is generally the same as a cream but without the water; it is nearly 100% oil or fat; (4) a gel, which is normally water only with maybe a little ethanol but without fat or oil; a thickening agent is added to provide the gel viscosity; (5) a foam, which is generally an emulsified type of cream; or (6) a solution or suspension of water or ethanol or a combination, such as described in the preferred formulations set forth above, without fat or oil, and with an emulsifier as needed. The pharmaceutical composition including the isopropyl myristate as the sole active ingredient is supplied in a form suitable for topical administration, such as those described above, alternatively a liniment, a paste, a stick, an aerosol, a shampoo, a soap, a hair conditioner, or a powder.

The components of the composition or formulation are blended and combined as known in the art. Additional customary inert or inactive additives known in the art may be added. See, for example, U.S. Pat. No. 4,933,330. The composition is applied as similar compositions are applied, preferably by spraying or rubbing into the area affected by psoriasis one, two or three times per day.

The known active agents for the treatment of psoriasis include the following: corticosteroids, calcipotriol, retinoid compounds, anthralin and its derivatives, zinc pyrithione, coal tar, salicylic acid, 4-aminosalicylic acid, 5-aminosalicylic acid, allantoin, hydrocortisone, juniper tar, birch tar, pine tar, vegetable tar, mineral tar, menthol, phenol, undecylenate compounds, spermidine, spermine, putrescine, 5-amino or substituted amino 1,2,3-triazoles, certain halomethyl derivatives of a-amino acids, certain phenyl alpha-acyloxyacetamide derivatives, imidazoles, resorcin, sulfur, ammoniated mercury, eosin, and occlusive watertight films. The invented compositions and formulations are free from the presence of each of these known active agents, and are free from the presence of all other known active agents for the treatment of psoriasis.

The following Examples further illustrate various aspects of the invention.

EXAMPLE 1

A 60 year old woman with long-standing psoriasis had symmetrical pink plaques on each forearm. She was treated for two weeks, with Formulation A mentioned above (40% concentration) on the right forearm and with Formulation B mentioned above (25% concentration) on the left forearm. Both forearms improved, the right forearm more thoroughly than the left. By the end of the two weeks, both areas were flatter and paler, the right forearm almost normal looking.

EXAMPLE 2

A 62 year old man had red, scaly patches of psoriasis on his scalp for more than 7 years. The affected areas, worst over both ears, were bright red, with thick yellow crusts and scattered follicular pustules. He was treated for three weeks with Formulation A and Formulation B sprayed from a pump spray bottle twice a day. At the end of three weeks, both treated areas had improved. The area over the left ear, treated with Formulation B, was less red, but still quite scaly. The area over the right ear, treated with Formulation A, was now colored only a very faint pink color, and the scale was a fine powdery white film. He requested further supplies of the product.

EXAMPLE 3

A 46 year old woman suffered from severe psoriasis that had required a one week hospitalization two months previously. When treated, her psoriasis was in a quiescent phase but with indolent, light-colored scaly plaques. She used Formulations A and B sprayed twice a day on affected areas. The spray burned and produced a stinging sensation for the first few days. She persisted with use and found the irritation less. By the start of the second week of treatment, all areas had started to clear, the Formulation A treatment area more than the Formulation B treatment area.

EXAMPLE 4

A 37 year old woman had difficult-to-control psoriasis for 13 years. She had annular-shaped pink plaques on both legs and both thighs. She was treated twice daily with sprays of Formulations A and B and showed improvement. Formulation A seemed to work better than Formulation B. After two weeks she ran out of product and saw the lesions begin to worsen again. She requested an additional supply.

EXAMPLE 5

A 76 year old man with psoriasis for 11 years had suffered a recent flare and could not clear his skin with conventional corticosteroid, calcipotriol or retinoid creams. He sprayed affected areas with Formulations A and B. The skin lesions did not go away but seemed slightly thinner. He requested a further supply.

The results of Examples 1–5 were surprising and unexpected.

Although the preferred embodiments have been described, it is understood that various modifications may be resorted to without departing from the scope of the invention as disclosed and claimed herein.

What is claimed is:

1. A method of treating psoriasis comprising topically administering to a human having psoriasis an effective amount of isopropyl myristate, said isopropyl myristate being present in a topically acceptable pharmaceutical composition, said isopropyl myristate being the only active ingredient for the treatment of psoriasis in said composition.

2. A method according to claim 1, said composition being at least 25 weight percent isopropyl myristate.

3. A method according to claim 2, said composition being at least 40 weight percent isopropyl myristate.

4. A method according to claim 2, said composition being 38–60 weight percent isopropyl myristate.

5. A method according to claim 1, said composition being at least 38 weight percent isopropyl myristate, at least 40 weight percent of said composition being water, ethanol, isopropyl alcohol, or any combination thereof.

6. A method according to claim 5, said composition being 38–60 weight percent isopropyl myristate, 1.5–10 weight percent water, and 35–60 weight percent ethanol.

7. A method according to claim 6, said composition further comprising an effective amount of emulsifier.

8. A pharmaceutical composition in a pump spray, said composition consisting essentially of 38–60 weight percent isopropyl myristate, 1.5–10 weight percent water, 35–60 weight percent ethanol, and an effective amount of emulsifier, said composition being effective for the treatment of psoriasis.

9. A composition according to claim 8, said emulsifier comprising sodium lauryl sulfate.

* * * * *